United States Patent [19]

Willits

[11] 4,434,793

[45] Mar. 6, 1984

[54] PELVIC STABILIZER

[76] Inventor: Charles A. Willits, 9791 La Cresta Cir., Huntington Beach, Calif. 92646

[21] Appl. No.: 294,906

[22] Filed: Aug. 21, 1981

[51] Int. Cl.³ .................. A61F 13/00; A61B 19/00
[52] U.S. Cl. ................................ 128/134; 128/133; 128/1 A
[58] Field of Search .............. 128/1 A, 133, 134, 99, 128/102, 105, 122; 297/464, 465, 467, 468, 484, 119/96; 434/247, 254, 255; 272/33 R, 49, 71

[56] References Cited

U.S. PATENT DOCUMENTS

| 1,238,380 | 8/1917 | Bellan | 434/254 |
| 1,587,605 | 6/1926 | Scroggins | 272/71 |
| 2,668,577 | 2/1954 | Vanderschel | 128/134 |
| 3,004,519 | 10/1961 | Weissman | 119/96 |
| 3,046,982 | 7/1962 | Davis | 128/134 |
| 3,152,802 | 10/1964 | Heisler et al. | 272/33 R |
| 3,199,626 | 8/1965 | Van Schaik et al. | 182/3 |
| 3,287,064 | 11/1966 | Freeman | 128/133 |
| 4,186,962 | 2/1980 | Meeker | 297/467 |
| 4,308,629 | 1/1982 | Freeman | 434/254 |

Primary Examiner—C. Fred Rosenbaum
Assistant Examiner—C. W. Shedd

[57] ABSTRACT

The invention described relates to a device which is especially useful in a substantially weightless environment. The particular device provides a means for fixing or stabilizing the pelvis of the user with respect to controls or equipment operated by the user in a substantially weightless condition. The apparatus permits both arms to be free for providing working movements in combination with the torso of the user.

12 Claims, 4 Drawing Figures

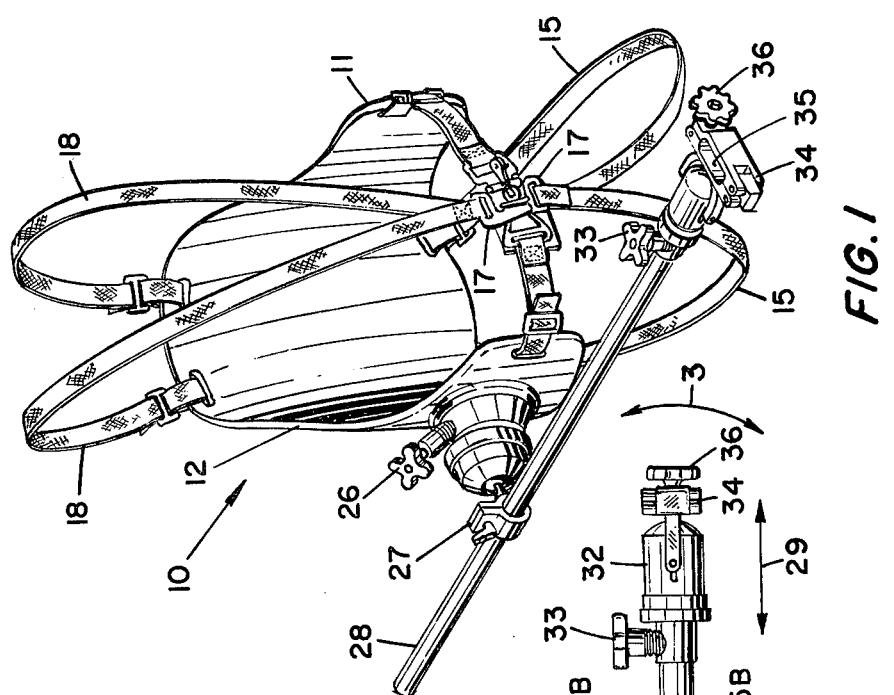
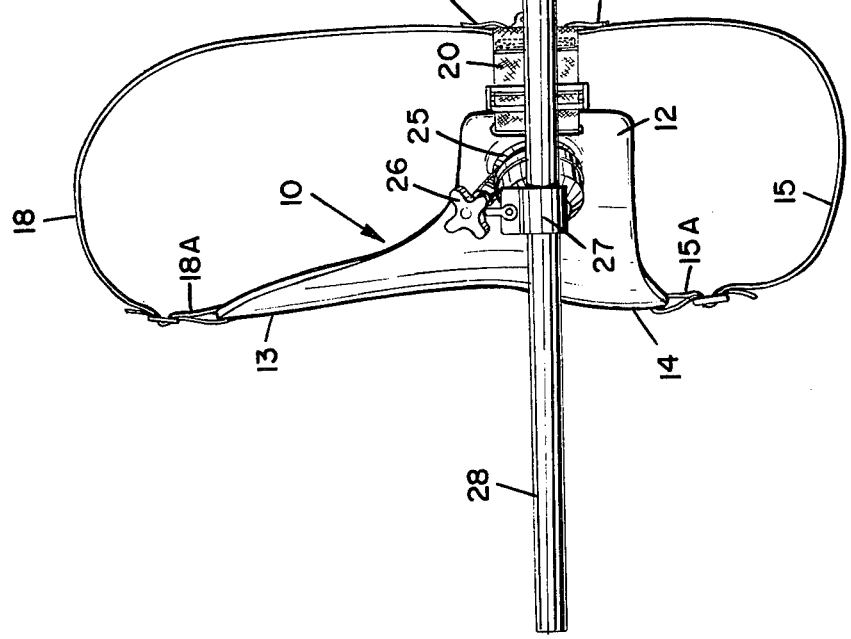

PELVIC STABILIZER

BACKGROUND

1. Field of the Invention

This invention is directed to a device which is, in general, useful in a substantially weightless condition or environment and, more particularly, a device which is useful by workers in such an environment, such as astronauts or aquanauts.

2. Prior Art

With the advent of space travel and exploration, many unique and previously unexpected situations and problems have developed. One of the significant problems is that, in a weightless (or substantially weightless) condition, certain working manipulations and movements are difficult, if not impossible, to perform compared to the same activity with earth's gravity present. For example, many activities which use primarily the arms and upper torso in a gravity condition, are not readily performed in a weightless condition inasmuch as the legs and lower torso provide no stabilizing effect or reactive surface or friction. That is, with gravity, the legs and/or feet act to provide the pelvis with a stable "platform" for a motion and action of the back, torso and arms interacting as a unit to generate working movements. Notably, these types of movements do not require the leg-flexing forces but do require the related traction imparted by the feet against the "floor". However, in the weightless or near-weightless environments of space or neutral-buoyancy underwater, the legs and feet combination have no such platform to attach to, react against or derive tractive friction from. Such surfaces to attach to, react against and give traction to the soles of the feet must be, at best, artificially supplied at every pre-determined worksite and related orientation(s), if, both hands are required to perform the work. Otherwise, one hand must grip a reactive/retaining structure to react the workloads and hold position. The requirement, to provide an artificial "piece-of-floor", leg-length removed from the equipment/surfaces man must manipulate within the premium pressurized volume of the space-craft (with its multiple functions) imposes severe design and volume use limitations on the interior spaces and surfaces.

Current practice (in earth gravity) dedicates flat "floor" surfaces in these volumes to be used with suction-cup platforms attached to the shoes. This then dictates that all work station surfaces must be facets of the surrounding wall perimeter of the pressurized volumes, and be a nominal leg length distance from the established "floor" surface. This practice is further compromised in volumetric requirements by the recent knowledge that the body's muscle structure renders the upright/vertical posture fatiguing, except for brief intervals, in the weightless environments. The neutral/comfort configuration/position of the body being near that in a chaise lounge with a head-elevating pillow.

The body accommodating envelope is no longer a convex oval tube but is a profile both convex and concave, with the foot element no longer at right angles (obtuse) to the lower leg. This body configuration further complicates the interior volumes and "floor" surfaces of the space vehicles and the functions these volumes enclose and define. There are provided hand holds/rails at intervals in the interior volumes for temporary positioning and moving about, but their use for work station positioning leaves only one hand free until the orientation is assumed to attach the feet to the "floor". However, this often is not achievable in the premium volumes.

A multiplicity of hand holds/rails in the manner of a "jungle gym" inside the limited volume is clearly an undesirable intrusion, so these aids (hand holds) are discretely and widely spaced for this reason and also because of the penalties of weight and structural requirements.

For the condition of "outside" the space vehicle's pressurized (atmospheric) volume, the suction-cup shoes will not function in the vacuum of space. Also, the restraint/positioning problem for working, pressure-suited in weightlessness is further complicated by the restricted movement of, notably the legs, and, to a lesser degree, the arms, as imposed by the pressure suit. Indeed, the astronaut must do muscle work against the suit to move out of the neutral position designed into the suit. Significantly, knee and leg-flexing are severely limited and demand muscle work by the astronaut to move to these out-of-neutral positions and to sustain them only briefly. This is notably true of the leg flexings. The useful and remaining suit movements for working manipulations are those of the torso and the arms in combination. This combination's effectiveness is, of course, prime because of the prehensile feature of the hands and their remaining sense of touch, with the important aspect that most of these manipulations can be within the astronaut's vision.

Current practice is to insert the pressure-suited astronaut's feet in a prepositioned "piece-of-floor" containing rigid, toe and heel traps which can be entered and exited by the gross positioning and movements of the pressure-suited astronaut's boots. This "piece-of floor", foot-trap must either be pre-positioned or designed into the "outside" site, or the foot-trap must be transported by the pressure-suited astronaut to the site and set up in a discrete orientation. However, the astronaut's prime means of locomotion near the space vehicle structure is hand-over-hand via hand holds/rails or via pre-strung tether lines. Therefore, anything he takes with him must be attached to him or be moved by him along a "slide-wife" for origin to destination, with the astronaut supplying the starting force, the controlled motion and finally the "braking force". Clearly, "piece-of-floor", foot-trap structures may not be provided within the aerodynamic envelope, external to the space vehicle, and at most, accessable attachments, below the surfaces, to which foot-trap structures may be attached, after transport to the site can only be achieved by significant penalties and energy of the pressure-suited astronaut's work schedules.

"Piece-of-floor" positioning requires a one-handed operation and hand holds in working proximity. If positioning adjustment is required in use, the astronaut must get out of the foot-trap, move "down" to the trap mount via hand holds to where he can reach it and observe it. Then he must reposition it with one hand, guess at its new position, climb "up" and re-enter the foot-trap again before work may be continued.

The alternatives of providing reacting "floor" surfaces (foot-traps) at every anticipated work site "outside" the space vehicle, or even inside the pressure volumes, are nearly impossible to very exacting, in their design penalties and certainly do not lend to any improvisation that might become necessary. Present methods and arrangements are inflexible, awkward, time consuming and necessarily expensive to use.

Clearly, an ideal solution is to provide a fully portable, readily variable, generally and rapidly adaptable positioning system expoiting the structure and configurations of existing and extendable hand hold/rail systems now necessary for hand-over-hand mobility both inside and "outside" the space vehicles. Such a system may well be adaptable to exploit the modular open-truss structures of large scale as currently envisioned for future space structures in near-earth orbits.

SUMMARY OF THE INSTANT INVENTION

This invention provides a rigid shell member which substantially encloses the lower back and the hips of that "shirt-sleeved" user inside the space vehicle's pressurized volume or that "wet-suited" aquanaut, neutrally-bouyant under water. It is retained and positioned on the torso by appropriate belts and straps.

In the case of the pressure-suited astronaut, the shell function is provided by the rigid upper torso of the suit and and can be used in combination with the Portable Life Support System (PLSS) back-pack attached to the upper torso shell and extending down to the lower back and around the hip sides.

In the "shirt-sleeve" and "wet-suit" casis (and with the pressure-suit case also) the torso is relatively free to bend forward and side-to-side, but backward movement is restricted.

Quick-release mounts are integrated with the shirt-sleeve/wet-suit shell or with the back-pack shell, over the hip-points. These mounts are easily reached and operated, and can be viewed by the wearer. The accept and grip adjustable-length hip-arms with locable, ball-joints at the hip-points. The "wrist"-ends of the "arms" have lockable, ball-joints which full-swivel on the arm-tubes. The wrist latches can allow the shirt-sleeve, wet-suit or pressure-suit astronaut/aquanaut to capture and latch, with that hand deploying the restraint's hip-arm, a selected variety of hald holds/rails while holding/positioning the body to the hand hold/rail with the other arm/hand.

Repositioning and adjusting is immediate, finely tuned, reachable, visible and is greatly variable because of the individually adjustable length-locks and the "hip" and "wrist" ball-joint locks. When worn by the astronaut/aquanaut but not in "use", the hip-arms are strapped to and move with the wearer's upper leg-length, a position which minimally affects body motion or its locomotion envelope in weightless translation or movements.

BRIEF DESCRIPTION OF THE DRAWINGS

FIG. 1 is a perspective view of the instant invention.
FIG. 2 is a side view of the instant invention.

DESCRIPTION OF A PREFERRED EMBODIMENT

Figure 4:
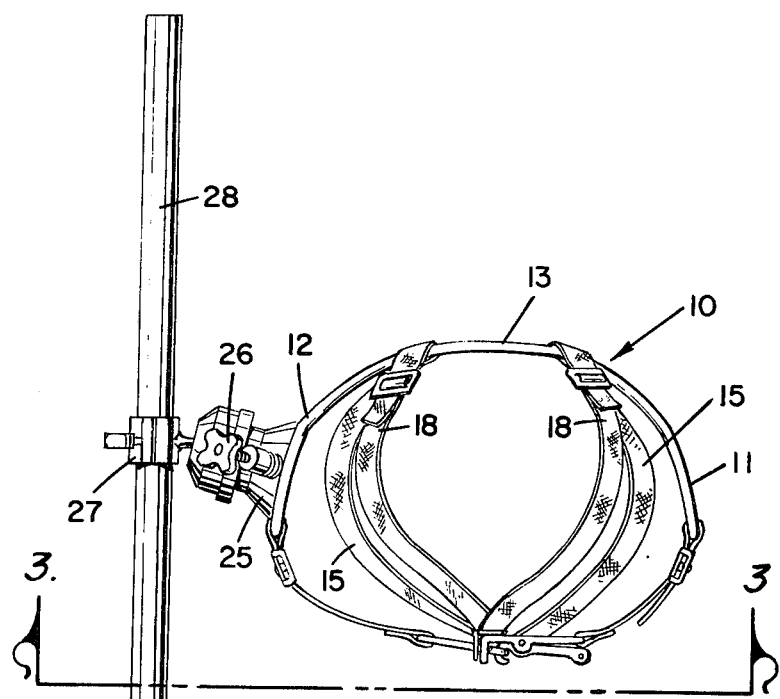
FIG. 4 is a top view of the instant invention.
Figure 3:
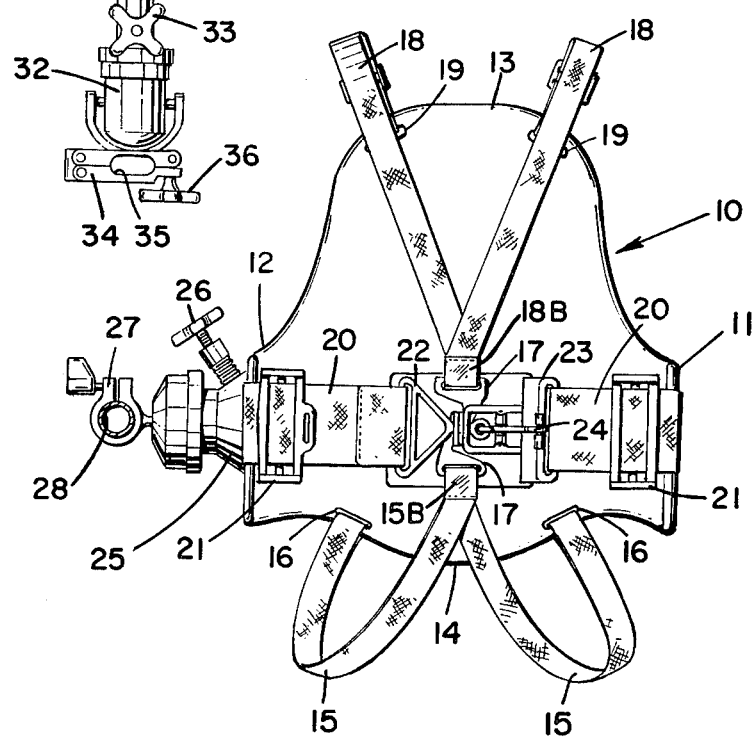
FIG. 3 is a front view of the instant invention.

Referring now to all the Figures concurrently, the shell 10 is configured so as to embrace the lower back and hip sides of the wearer. The shell 10 includes left hip portion 11 and the right hip portion 12. The upper back portion 13 and the lower back portion 14 are, of course, portions thereof as well. It will be seen that the hip portions 11 and 12 substantially embrace the hip of the wearer while the upper back portion 13 rides part way up the back of the wearer, typically below the clavicle but in proximity to the lower rib cage. The lower portion 14 engages the upper buttock and tailbone portion of the wearer.

Shell 10 is formed of any suitable lightweight, rigid material which can be formed in the appropriate shape. Typical, but not limitative of the invention, the shell can be formed of material such as fiber-reinforced composite materials. In a preferred embodiment, the shell 10 is formed of an electrically insulative material to prevent inadvertent short circuits when the user is wearing the device. Similarly, the device can be substantially thermally non-conductive for the comfort of the wearer.

In the preferred embodiment, the shell includes a plurality of slots or notches for receiving straps or the like. In a typical case, the straps can be fabricated of any materials suitable to the operative environments. For example, a pair of belts 15 are looped through slots 16 in the lower portion 14 of the shell 10. The ends 15A of the straps are reversed on themselves and joined together through suitable means such as sewing, weaving, riveting or the like. The other ends of straps 15 are joined together at common joint 15B and are arranged to engage a portion of clasp 17.

Clasp 17, as shown in the embodiment herein, is only one type of suitable quick-release fittings of clasp which can be provided. Clasp 17 is shown only for illustrative purposes and is not intended to be limitative of the type of clasp which can be used with the invention.

A further pair of straps 18 is provided and associated with the upper portion of shell 10. In particular, the ends 18A of strap 18 are reversed upon themselves and joined in similar manner to the strap ends 15A. These strap ends can be welded, riveted, stitched or the like. Strap ends 18A are arranged to engage slots 19 in the upper portion 13 of shell 10. Again, the other ends of the straps 18 are joined together at a common point 18B and associated with clasp 17.

In a similar manner, waist or girdle straps 20 are arranged to engage with the hip portions 11 and 12, respectively. In the case of belts 20, suitable adjustment fasteners 21 are provided in order to permit adjustment of the length of straps 20 to accommodate the girth of different personnel. Moreover, this belt is usually more critical in the adjustment thereof. Of course, the other belts 15 and 18 can include length adjustment cinches if deemed desirable.

The ends of belts 20 are also connected to latch portions 22 and 23 which are also used to engage clasp 17 in order to join together the belts 15, 18 and 20 at a common fastening or closing device. By the simple expedient of releasing hook 24 from the eye in clasp 22, the closure device (clasp) comes apart and the entire belt system is released so that the wearer can remove the entire shell apparatus with a single action. A typical, but not limitative, example is a quick-release parachute harness hardware.

At one of the hip sides, in this example hip side 12, there is provided a hip joint 25 which comprises a known type of the valve handle 26, pressure is applied to the hydraulic fluid within the ball joint 25. Thus, the ball joint is, selectively, maintained by this force multiplication in a fixed position. By operating the valve handle 26 in the opposite direction, pressure is released in the ball joint 25 and the ball joint is free to move to another selected position.

Maintained in a clamping device 27 which is supported by ball joint 25 is arm tube 28. The position of arm tube 28 is controlled as a function of the clast 27 and ball joint 25. That is, as suggested relative to FIG. 2, arm 28 can be moved backward and forward (see arrow 29) when clamp 27 is loosened. Of course, once the clamp is tightened, arm tube 28 is fixed in position relative thereto. The arm length may telescope and lock for length adjust also, as is suggested by arrows 30 and 31 (FIGS. 2 and 4, respectively), the arm tube 28 can move upwardly or downwardly or inwardly or outwardly relative to the shell 10. In point of fact, with the use of ball joint 25, the arm tube 28 can be positioned in virtually any position desired. Once the appropriate position is achieved, valve handle 26 is turned so as to apply hydraulic pressure wherein ball joint 25 is locked in the chosen position.

In addition, a suitable hydraulic ball joint "wrist" 32 is provided on at least one end of arm tube 28. This ball-joint lock includes a valve handle 33 which is used to control the hydraulic pressure and, thus, positioning associated with the wrist 32. Again, an essentially global positioning capability is provided by this ball joint. Fastened to or associated with ball joint 32 is a suitable clamping device 34. The clamp 34, as shown in the preferred embodiment, includes a pair of hinged plates which have a mutually aligned groove therein to produce a channel therebetween when the hinged plates are closed in parallel connection. The channel 35 is used to encompass and engage a rail or the like which can be provided in the vehicle in question. This rail may be a specially provided rail for gripping or grasping by the apparatus of the instant invention. On the other hand, the rail may be a structural portion of an existing device in the vehicle. In the illustrative embodiment, a screw clamp 36 is used to maintain the plates of clamp 34 in a closed relation thereby to form a secure holding element.

It must be understood of course that the clamp 34 may be replaced by any number of similar clamps such as a clamp which has an over center linkage wherein the clasp automatically closes and locks when the linkage is activated by placement of the clamp against a rod or the like. Other clasps or grips may be arranged to conform to the palm of the hand of the user wherein the user can merely place the clamp adjacent the support structure and then close the clamp by gripping the same with the hand. The type of clamp at the outer end of the arm tube is a portion of the invention only insofar as a clamping element is required for a variety of handhold-/rail cross sections. The specific type of clamping element is not a portion of the invention, per se.

In operation, the user straps on the stabilizer apparatus with the hip sides 11 and 12 adjacent the wearers hips and with the bottom portion 14 adjacent the tailbone and the upper portion 13 adjacent the small of the back of the wearer. The shoulder straps and the leg straps are brought together with the waist straps and joined at the common "quick-release" latch device. The hip-arm tube 28 is then adjusted relative to both clamp 27 and hip-joint 25. When worn but not in use or for weightless locomotion, the hip-arm is strapped to and moves with the upper leg-length. The clamp 34 is then positioned adjacent the appropriate support structure and the respective clamps are secured. With the types of clamps involved, a very strong, rigid position is achieved relative to the basic support structure engaged by clamp 34. Thus, support shell 10 is effectively immobile with respect to the vehicle structure. Inasmuch as the wearer of the unit is strapped into the shell, the pelvic area of the user is also relatively immobile. This reactive surface(s) permits the wearer to perform tasks which use arms or upper torso (or, for that matter, legs and the lower torso irrespective of the gravity conditions in the ambient).

When the user wishes to relocate to another area of the vehicle of the like, the appropriate clamps are loosened. For example, clamp 34 can be removed from the secure anchoring position and moved to another location in that is all that is desired. On the other hand, clamp 34 can be removed, hip joint 25 can be rotated and the like. In the event that the wearer wishes to traverse a significant distance, the arm tube can be left in a relatively slack position, i.e., hip joint 25 is left basically unpressurized, and the arm tube 28 can be strapped or affixed to the upper leg portion of the wearer. Thus, the entire mechanism is under control and not in the way or randomly moving about. Moreover, it can be seen that with the global or universal positioning of the hip joint 25, a full three dimensional range of positions can be achieved by the wearer, vis a vis, the anchor point associated with clamp 34.

By using the hydraulic ball-joints locks, a force multiplication can be achieved very easily wherein large forces or weights can be tolerated by the apparatus without altering the discrete geometrical set of the unit.

It should be clear that additional modifications can be used with the system. For example, the arm tubes 28 could be telescoping tubes locked to each other in order to achieve greater range or less rearward intrusion when close-up to attachments. As noted, different types of clams 34 can be used at the ends of arm tubes 28. Different types of materials can be used for any of the elements described. In fact, it is expected that space age technology will provide materials not currently available which will have advantageous characteristics such a high strength, low weight, and so forth, all of which will enhance the characteristics of the invention. As noted, the fasteners or means for fastening straps or belts and so forth, can all be modified to achieve the most desirable combination. The materials shown and/or described in this application are not a part of the invention, per se, but are illustrative only. These materials are not intended to be limitative of the invention in any way. Any modifications of the type suggested and which fall within the purview of this description are intended to be included herein as well. The scope of the invention is limited only by the claims appended hereto.

Having thus described a preferred embodiment of the instant invention what is claimed is:

1. A device usable in diverse environments for positioning a worker adjacent to a structure in such a fashion that said worker can perform useful tasks, said device comprising:

a shaped, rigid reaction surface adapted to generally conform to the back of said worker; said surface having extensions adapted to overlie the hip areas of said worker;

fastening means for securing said surface to said worker;

a single stabilizer arm having a proximal end, a proximal portion, and a distal end;

at least one of said extensions having an adjustable connector attached thereto which is releasably connectable to said proximal portion;

clamp means at said distal end for providing attachment to said adjacent structure, whereby, the orientation of the worker is adjustably securable by said worker with respect to said structure.

2. The device of claim 1 wherein said surface comprises a portion of a pressure-suit for an astronaut.

3. The device of claim 1 wherein said surface comprises a back-pack shell suitable for underwater usage by an aquanaut.

4. The device of any one of claims 1, 2, or 3 wherin said connector comprises a quick-release joint which may be alternately connected to either of said extensions.

5. The device of claim 4 wherein said connector further comprises a spherically adjustable joint with lock means for locking said connector at any given position within a range of positions.

6. The device of claim 5 wherein said lock means is hydraulically actuated.

7. The device of claim 6 wherein said arm has a diameter less than 1.50 inches (about 38 mm) and has a gripping means on said proximal portion for enhancing gloved-hand gripping.

8. A device usable in diverse environments for positioning a worker adjacent to a structure in such a fashion that said worker can perform useful tasks, said device comprising:

a shaped reaction surface for the torso of said worker;

fastening means for securing said surface to said worker;

a single stabilizer arm having a proximal end, a proximal portion, and a distal end;

said surface having an adjustable connector attached thereto which is releasably connectable to said proximal portion;

clamp means at said distal end for providing attachment to said adjacent structure, whereby, the orientation of the worker is adjustably securable by said worker with respect to said structure.

9. The device of claim 1 whereby said stabilizer arm comprises a single, rigid, adjustable-length arm having a proximal end, a proximal portion, and a distal end.

10. The device of claim 8 wherein said connector comprises a quick-release joint which may be alternately connected to more than one site on said surface.

11. The device of claim 1 or 8 wherein said clamp means further comprises a spherically adjustable joint with lock means for locking said clamp means to said stabilizer arm's distal end in any given position within a range of positions.

12. The device of claim 1 wherein said lock means is hydraulically actuated.

* * * * *